Figure 1:
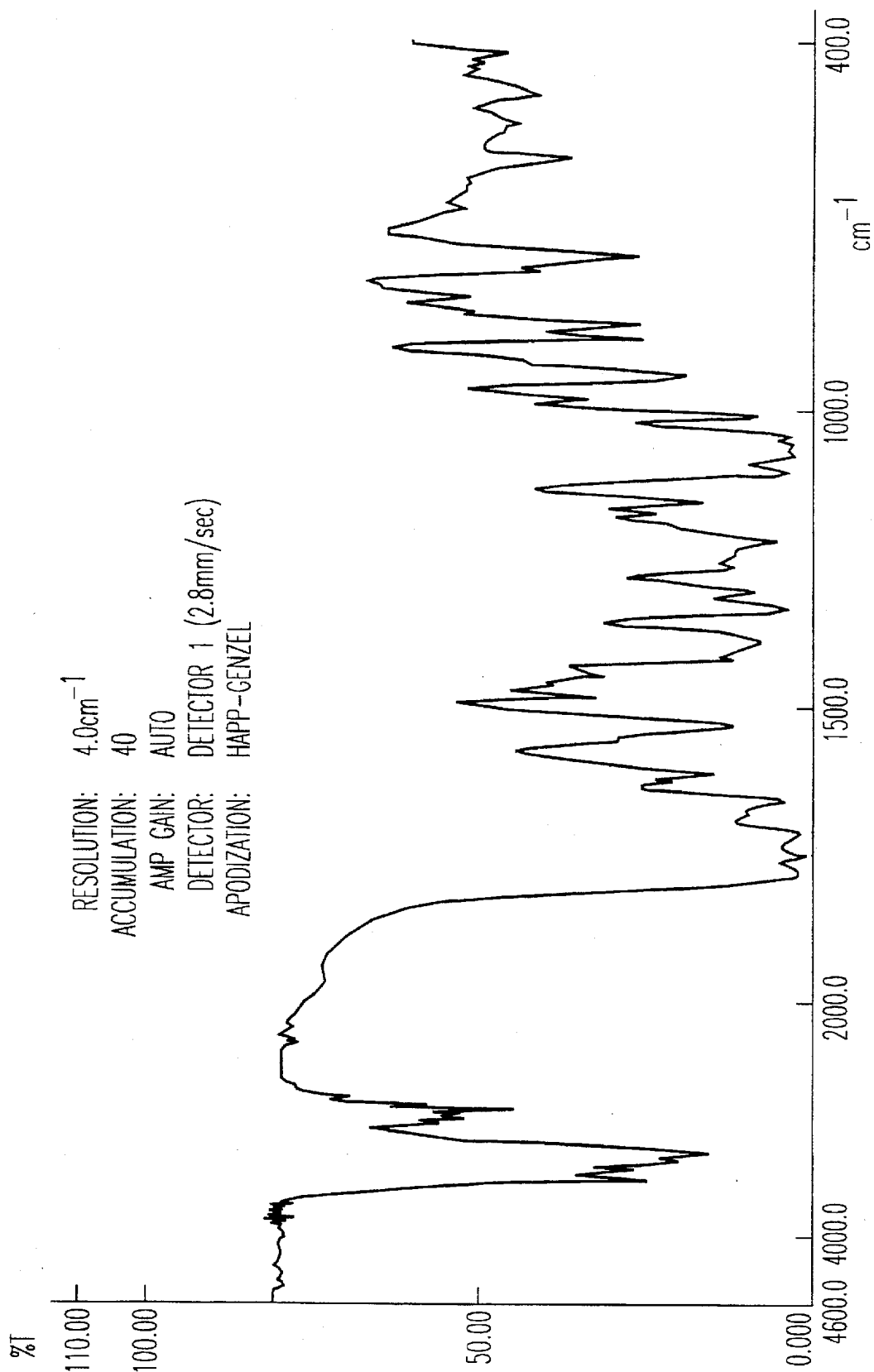

United States Patent [19]
Zenoni et al.

[11] Patent Number: 5,677,443
[45] Date of Patent: Oct. 14, 1997

[54] BIOAVAILABLE CRYSTALLINE FORM OF CEFUROXIME AXETIL

[75] Inventors: Maurizio Zenoni, Paullo; Mario Leone, Pioltello; Angelo Cattaneo, Monte Marenzo; Leonardo Marsili, Pessano, all of Italy

[73] Assignee: ACS Dobfar S.p.A., Tribiano, Italy

[21] Appl. No.: 664,552

[22] Filed: Jun. 17, 1996

[30] Foreign Application Priority Data

Aug. 3, 1995 [IT] Italy ................... MI95A1716

[51] Int. Cl.⁶ .................................. C07D 501/00
[52] U.S. Cl. .................................. 540/215
[58] Field of Search ........................... 540/215

[56] References Cited

U.S. PATENT DOCUMENTS 5,063,224  11/1991  Mosher et al. .................. 514/202

FOREIGN PATENT DOCUMENTS

| 0 107 276 | 3/1985 | European Pat. Off. |
| 2 340 950 | 9/1977 | France. |
| 2 549 837 | 2/1985 | France. |
| 3427828 | 7/1984 | Germany. |

*Primary Examiner*—Matthew V. Grumbling
*Assistant Examiner*—Michael Bucknum
*Attorney, Agent, or Firm*—Oblon, Spivak, McClelland, Maier & Neustadt, P.C.

[57] ABSTRACT

A bioavailable crystalline form of cefuroxime axetil, obtained by treating known crystalline or amorphous cefuroxime axetil with water or with a water-miscible organic solvent or with a mixture thereof at a temperature of between +20° C. and +100° C., followed by cooling and separating the crystalline product by known methods.

4 Claims, 3 Drawing Sheets

BIOAVAILABLE CRYSTALLINE FORM OF CEFUROXIME AXETIL

This invention relates to a bioavailable crystalline form of cefuroxime axetil, ie of (6R,7R)-3-carbamoyloxymethyl-7-[(Z)-2-(fur-2-yl)- 2-methoxyiminoacetamido]-3-cephem-4-carboxylic acid 1-acetoxyethylester.

Cefuroxime is a known product, its preparation being described in U.S. Pat. No. 3,974,153. It has a good spectrum of antibacterial activity, extending both to gram positive and gram negative microorganisms.

Cefuroxime cannot be used as such for oral administration, because it is not absorbed and does not enter the body fluid circulation.

Cefuroxime axetil is a promedicament for oral administration having high stability against β-lactamase producer strains. In this respect, once the ester has been absorbed and has entered the body fluid circulation, it is hydrolyzed to release cefuroxime, which is actually responsible for the antibacterial activity.

Example 1 of GB-A-1571683 describes for the first time the preparation of cefuroxime axetil in a crystalline form known hereinafter as the "a crystal": the characterisation of the α crystal by IR is subsequently given totally with reference to Example 1 of GB-A-2145409 of Glaxo Group Ltd.

The a crystalline form of cefuroxime axetil does not however possess the necessary bioavailability characteristics, whereas it is known that orally administered cephalosporins (and medicaments in general) must be in a highly bioavailable form.

In this respect, commercially available cefuroxime axetil registered throughout the world is in substantially amorphous form, as described and claimed in U.S. Pat. No. 4,562,181 in the name of Glaxo Group Ltd., which states that "the crystalline product"(α crystal) "does not possess the best balance of properties for commercial use"(col. 2, lines 3–6) whereas "the substantially amorphous form has a higher bioavailability following oral administration than the crystalline form"(col. 2, lines 10–15). In this respect it should be noted that, as recognized by Glaxo in its patent U.S. Pat. No. 4,562,181, in general the crystalline forms have the best balance between physico-chemical and biological properties and good stability, both during storage and marketing (col. 1, lines 57–61).

As is apparent from the subsequent Example 1 which forms part of this description, the procedure described in Example 1 of GB-A-2145409 and in Preparation 2 of U.S. Pat. No. 4,562,181 has been faithfully followed, to obtain cefuroxime axetil in a crystalline form, for which IR analysis was carried out in KBr. This IR analysis is confirmed, particularly within the region between 1000 and 500 $cm^{-1}$, by the spectrum published in the cited patent, showing substantial identity between the two IR spectra.

Hence even today, notwithstanding the studies carried out throughout the world in this field, only the α crystalline form of cefuroxime axetil (which is not bioavailable) and the substantially amorphous form (which is bioavailable) are known.

According to the present invention, it has been surprisingly found that if cefuroxime axetil in α crystalline form or in substantially amorphous form is treated with a mixture of water and a water-miscible organic solvent in the weight ratio of between 100:0 and 0:100 at a temperature of between +20° C. and 100° C. followed by cooling, a cefuroxime axetil in crystalline form is obtained which is different from the α crystalline form and is known hereinafter as the β crystalline form or β crystal. Again surprisingly, it has been found that the β crystal has good bioavailability characteristics which make it suitable for use in therapy, with an excellent balance between physico-chemical and biological properties and good stability during storage and marketing as stated by Glaxo in its patent U.S. Pat. No. 4,562,181.

As will be seen in the ensuing experimental part, the IR spectrum of the β crystal was obtained by the same method as for the α crystal. It was thus found that the two IR spectra are substantially different from each other, particularly within the region between 1000 and 500 $cm^{-1}$.

For greater certainty, the XR spectra were also obtained for both the α and β crystals, so decisively showing their different structure.

The reactions illustrated in the ensuing examples were followed by HPLC (mobile phase: 30% acetonitrile, 70% 0.03M phosphate buffer; Lichrospher column RP60 Select B 5µ temperature controlled at 45° C.; UV detector 270 nm; elution 1.7 ml/min.)

The IR spectra were obtained in the solid state (in KBr tablets) using an FT-IR 8101M SHIMADZU apparatus.

The X-ray diffraction spectra were determined on the powdered crystals using a PHILIPS PW 1710 diffractometer emitting radiation at wavelengths of 1.54051 Å and 1.54433 Å, produced by an X-ray tube with a copper anode, at a generator voltage of 40 KV and a current intensity of 40 mA at the generator.

The samples subjected to examination were mounted in a NISKAMEN sample carrier to prevent preferential orientation. The data obtained were collected after calibrating the apparatus with an external standard, the reading and the graphical construction of the spectrum being executed with an ADP 3.6 PC program.

EXAMPLE 1

The α crystalline form was synthesized by following as faithfully as possible the preparation described in Example 1 of GB-A-2145409 and in Preparation 2 of U.S. Pat. No. 4,562,181. In this manner, 12.5 g of (R,S)-1-acetoxyethyl-bromide were prepared by reacting 3.30 g of acetaldehyde with 9.20 g of acetylbromide in 30 ml of DMAC and 12 mg of anhydrous zinc chloride for 4 hours at −10° C. The solution prepared in this manner was added to a stirred suspension of 20 g of sodium cefuroxime in 80 ml of DMAC. The reaction was conducted for 90 minutes at −1° C. with the addition of 0.5 g of potassium carbonate, and left to come to completion for a further two hours at between +1 and +3° C. The mixture was then added rapidly to a mixture of 200 ml of ethylacetate and 200 ml of a 3% solution of sodium bicarbonate. After stirring for one hour the organic phase was separated, washed again with 100 ml of a normal solution of hydrochloric acid and then with 30 ml of a 20% solution of NaCl containing 2% of sodium bicarbonate. All these aqueous phases were pooled and re-extracted with 100 ml of ethyl acetate, the pooled organic phase being decoloured with carbon (2 g) at ambient temperature for 30 minutes. After filtration the solvent was removed under vacuum at 20° C., the system concentrated to 150 g and stirred for one hour at ambient temperature until substantial crystallization was obtained. 250 ml of diisopropyl ether were added slowly (45 minutes) and stirring continued for one hour. The product was filtered off under vacuum and washed with a 1:2 acetate/ether mixture. The product when dried under vacuum at 50° C. provided a product, a sample of which (identified as 115/5 FP) proved to have the IR and XR spectra shown in the accompanying FIGS. 1 and 2 respectively, characteristic of the α crystal.

Figure 2:
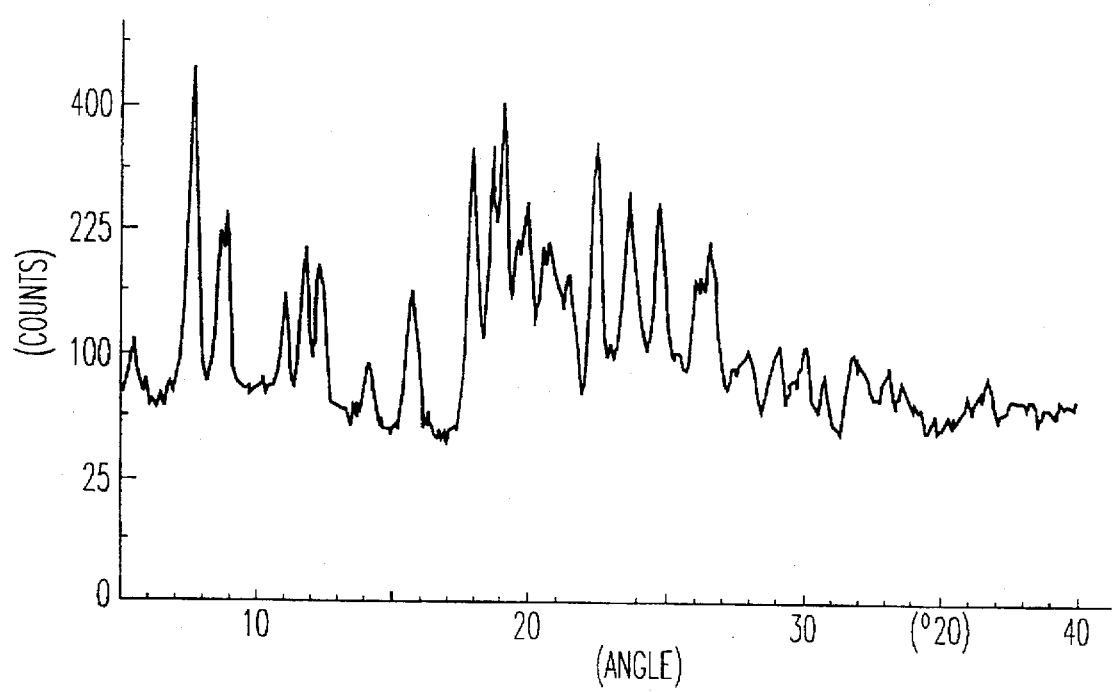

In FIG. 1 the horizontal axis indicates cm$^{-1}$, and the vertical axis indicates percentage transmittance (%T). In FIG. 2 the horizontal axis indicates the angle whereas the vertical axis indicates the peak intensity.

From FIG. 2 it can be seen that the X-ray diffraction spectrum of the α crystal has the following characteristics.

| Angle (°2θ) | Relative Intensity (%) |
| --- | --- |
| 5.555 | 18.1 |
| 5.850 | 7.7 |
| 7.770 | 100.0 |
| 8.765 | 39.6 |
| 9.055 | 42.0 |
| 11.120 | 23.2 |
| 11.855 | 34.4 |
| 12.525 | 26.2 |
| 14.160 | 13.3 |
| 15.695 | 23.2 |
| 17.950 | 63.4 |
| 18.170 | 45.3 |
| 18.725 | 66.4 |
| 19.140 | 85.7 |
| 19.590 | 37.3 |
| 20.025 | 49.5 |
| 20.600 | 36.6 |
| 20.860 | 38.1 |
| 21.485 | 27.5 |
| 22.565 | 67.4 |
| 23.815 | 47.8 |
| 24.900 | 50.4 |
| 26.075 | 23.8 |
| 26.700 | 35.1 |
| 28.015 | 13.3 |
| 29.170 | 11.5 |
| 30.235 | 10.3 |
| 30.830 | 6.7 |
| 31.780 | 15.1 |
| 33.120 | 9.9 |
| 33.735 | 6.7 |
| 36.695 | 6.7 |
| 40.850 | 8.1 |
| 43.870 | 4.7 |
| 46.505 | 3.2 |
| 54.590 | 0.0 |
| 55.640 | 1.4 |
| 57.215 | 3.2 |
| 58.135 | 4.4 |

EXAMPLE 2

The α crystal obtained in Example 1 is transformed into the β form by the following method: 15 g of α cefuroxime axetil are suspended in 150 ml of water, the system is heated to 40° C. for three hours, the product filtered off under vacuum and washed with water. The product obtained is dried under vacuum at 40° C. to obtain 14 g of a solid product (β crystal) showing the same R/S as the starting product. A sample of the crystalline product of β form obtained in this manner (identified as 104/5 FP) was analyzed to give the IR spectrum shown in FIG. 3 and the XR spectrum shown in FIG. 4. The horizontal and vertical axes indicate the same quantities as in FIGS. 1 and 2.

It can be seen that the X-ray diffraction spectrum of the β crystal has the following characteristics.

| Angle (2θ) | Relative Intensity (%) |
| --- | --- |
| 7.585 | 35.7 |
| 8.200 | 15.3 |
| 9.195 | 62.9 |
| 9.405 | 6.3 |

-continued

| Angle (2θ) | Relative Intensity (%) |
| --- | --- |
| 10.385 | 21.5 |
| 11.875 | 23.6 |
| 12.530 | 62.0 |
| 12.605 | 53.6 |
| 12.840 | 19.5 |
| 13.960 | 19.0 |
| 14.460 | 7.2 |
| 14.870 | 2.8 |
| 15.535 | 10.1 |
| 15.895 | 29.4 |
| 16.270 | 17.1 |
| 16.545 | 12.8 |
| 16.910 | 68.4 |
| 18.270 | 71.2 |
| 18.830 | 21.5 |
| 19.135 | 25.8 |
| 19.680 | 14.0 |
| 20.500 | 28.8 |
| 21.260 | 100.0 |
| 21.930 | 28.8 |
| 22.495 | 31.8 |
| 22.785 | 36.4 |
| 23.080 | 19.0 |
| 23.565 | 14.4 |
| 24.865 | 46.5 |
| 25.425 | 42.7 |
| 26.225 | 15.7 |
| 26.880 | 14.4 |
| 27.950 | 10.1 |
| 28.910 | 11.2 |
| 30.270 | 8.8 |
| 30.965 | 10.5 |
| 31.990 | 8.4 |
| 32.405 | 5.0 |
| 33.340 | 3.6 |
| 34.820 | 17.6 |
| 36.355 | 5.5 |
| 37.500 | 4.3 |
| 38.560 | 5.0 |
| 39.320 | 6.6 |
| 40.590 | 3.4 |
| 41.300 | 3.0 |
| 42.360 | 4.3 |
| 43.410 | 5.0 |
| 44.840 | 2.3 |
| 46.605 | 2.6 |
| 49.615 | 1.1 |
| 51.045 | 1.2 |
| 52.620 | 2.3 |

EXAMPLE 3

Figure 4:
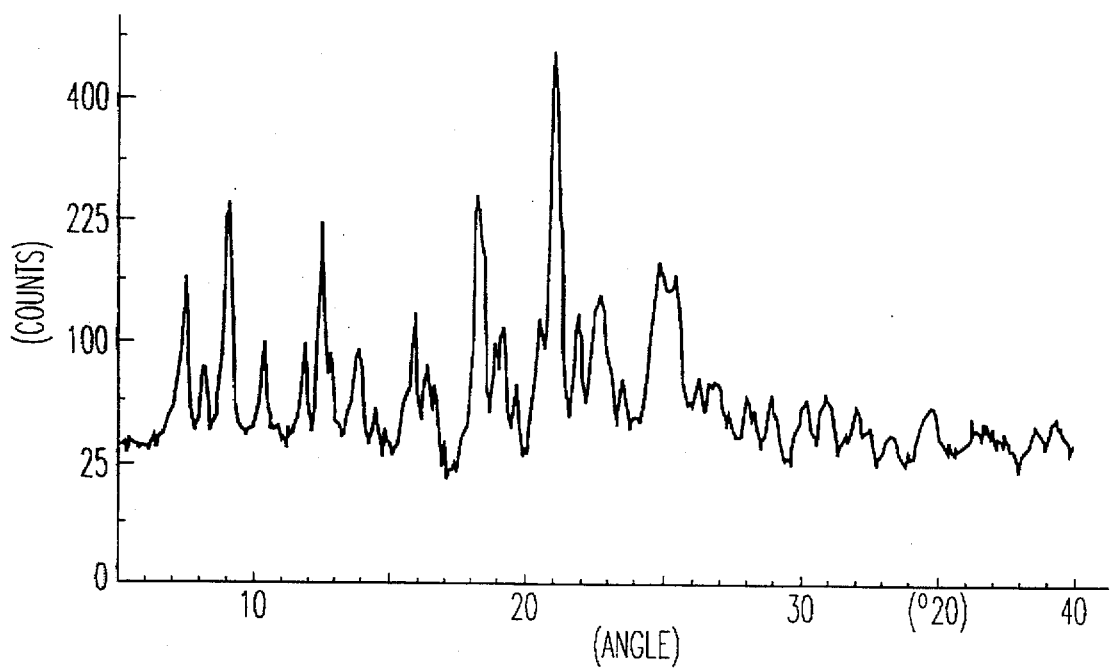
Figure 3:
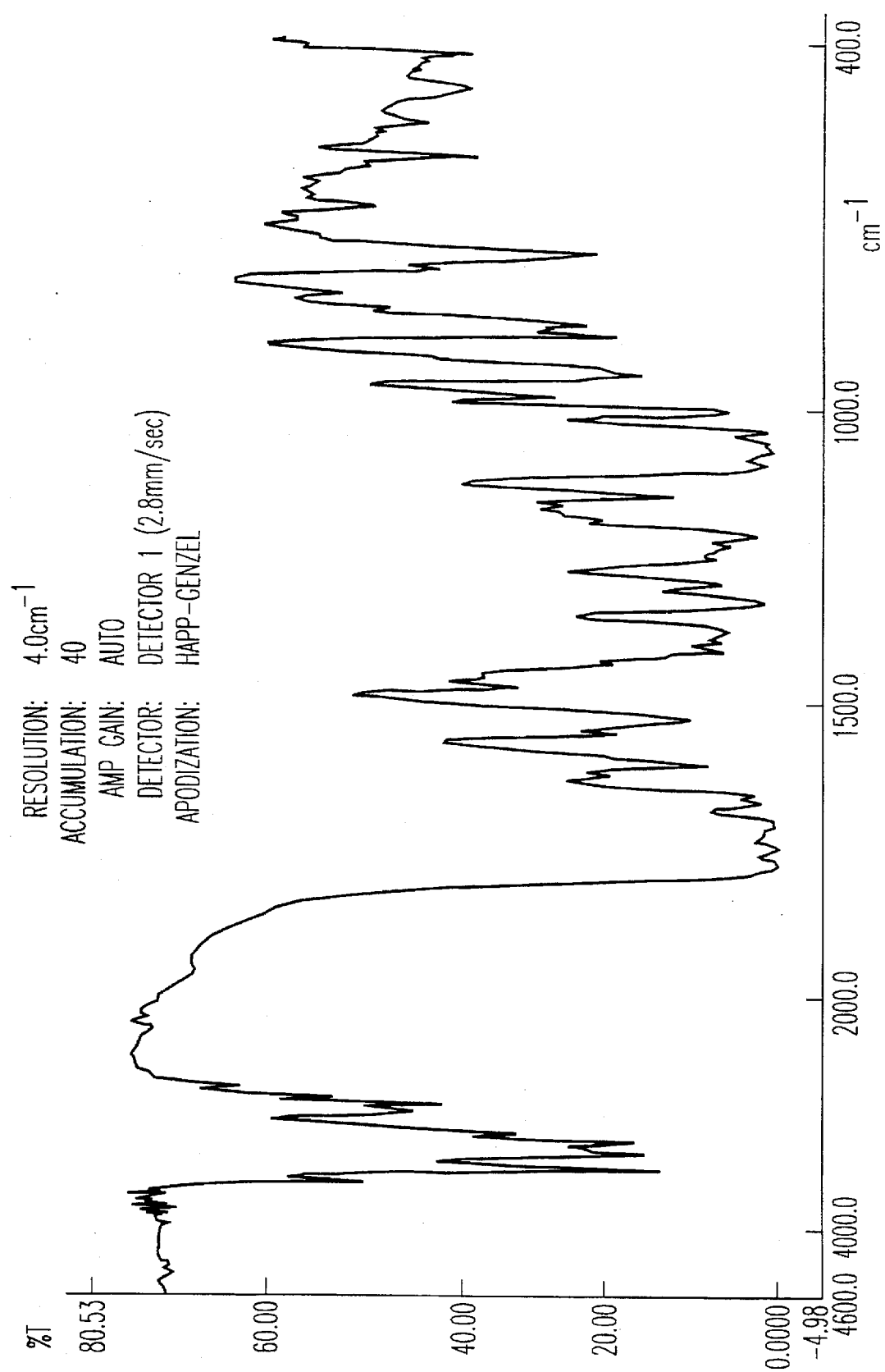

20 g of cefuroxime axetil (prepared by the method reported in GB-A-1571683) are dissolved in 500 ml of methanol at 40° C.; while maintaining this solution hot, 1000 ml of water maintained at 40° C. are slowly added. When the addition is complete the system is cooled to ambient temperature and filtered under vacuum, washing the product with water. The dried product (13.5 g) has an R/S ratio of 0.85:1 whereas the starting product had an R/S ratio of 0.94:1. The solid (β crystal) shows an IR and XR profile different from the starting product, as indicated in FIG. 3 and 4.

EXAMPLE 4

50 g of spray-dried cefuroxime axetil in substantially amorphous form are suspended in 500 ml of water and heated to 40° C., maintaining stirring for three hours. The system is cooled to ambient temperature and filtered, washing the product with water. The dried solid provides 46 g of product which on IR and XR analysis shows transformation into the β crystal. The R/S ratio is 1.2/1.0.

EXAMPLE 5

5 g of amorphous cefuroxime axetil (obtained by the procedure described in Example 22 of U.S. Pat. No. 4,562, 181) are treated at 40° C. for three hours with 50 ml of water. The dried product (4.8 g) has an R/S ratio of 0.64 and an IR spectrum similar to that shown in FIG. 3 (β crystal).

We claim:

1. A bioavailable crystalline form of cefuroxime axetil having the following X-ray spectrum:

| Angle (2θ) | Relative Intensity (%) |
| --- | --- |
| 7.585 | 35.7 |
| 8.200 | 15.3 |
| 9.195 | 62.9 |
| 9.405 | 6.3 |
| 10.385 | 21.5 |
| 11.875 | 23.6 |
| 12.530 | 62.0 |
| 12.605 | 53.6 |
| 12.840 | 19.5 |
| 13.960 | 19.0 |
| 14.460 | 7.2 |
| 14.870 | 2.8 |
| 15.535 | 10.1 |
| 15.895 | 29.4 |
| 16.270 | 17.1 |
| 16.545 | 12.8 |
| 16.910 | 68.4 |
| 18.270 | 71.2 |
| 18.830 | 21.5 |
| 19.135 | 25.8 |
| 19.680 | 14.0 |
| 20.500 | 28.8 |
| 21.260 | 100.0 |
| 21.930 | 28.8 |
| 22.495 | 31.8 |
| 22.785 | 36.4 |
| 23.080 | 19.0 |
| 23.565 | 14.4 |
| 24.865 | 46.5 |
| 25.425 | 42.7 |
| 26.225 | 15.7 |
| 26.880 | 14.4 |
| 27.950 | 10.1 |
| 28.910 | 11.2 |
| 30.270 | 8.8 |
| 30.965 | 10.5 |
| 31.990 | 8.4 |
| 32.405 | 5.0 |
| 33.340 | 3.6 |
| 34.820 | 17.6 |
| 36.355 | 5.5 |
| 37.500 | 4.3 |
| 38.560 | 5.0 |
| 39.320 | 6.6 |
| 40.590 | 3.4 |
| 41.300 | 3.0 |
| 42.360 | 4.3 |
| 43.410 | 5.0 |
| 44.840 | 2.3 |
| 46.605 | 2.6 |
| 49.615 | 1.1 |
| 51.045 | 1.2 |
| 52.620 | 2.3. |

2. A bioavailable crystalline form of cefuroxime axetil as claimed in claim 1, characterised by consisting of a mixture of R/S diastereoisomers in a ratio of between 0:1.0 and 1.0:0.

3. A bioavailable crystalline form of cefuroxime axetil as claimed in claim 2, characterised in that said diastereoisomer ratio in the mixture is between 0.9:1.1 and 1.1:0.9.

4. A process for producing a bioavailable crystalline form of cefuroxime axetil in accordance with claim 1, characterised in that cefuroxime axetil in α crystalline form or in substantially amorphous form is treated with a mixture of water and a water-miscible organic solvent in a weight ratio of between 100:0 and 0:100 at a temperature of between +20° C. and 100° C. for a time of between a few minutes and several hours, followed by cooling and isolating the crystalline compound.

* * * * *